(12) United States Patent
Asaoka et al.

(10) Patent No.: US 11,291,360 B2
(45) Date of Patent: Apr. 5, 2022

(54) VISUAL FIELD TEST ASSISTANCE APPARATUS

(71) Applicant: THE UNIVERSITY OF TOKYO, Tokyo (JP)

(72) Inventors: Ryo Asaoka, Tokyo (JP); Hiroshi Murata, Tokyo (JP)

(73) Assignee: THE UNIVERSITY OF TOKYO, Tokyo (JP)

( * ) Notice: Subject to any disclaimer, the term of this patent is extended or adjusted under 35 U.S.C. 154(b) by 490 days.

(21) Appl. No.: 14/771,150

(22) PCT Filed: Aug. 30, 2013

(86) PCT No.: PCT/JP2013/073426
§ 371 (c)(1),
(2) Date: Aug. 27, 2015

(87) PCT Pub. No.: WO2014/132470
PCT Pub. Date: Sep. 4, 2014

(65) Prior Publication Data
US 2016/0015263 A1 Jan. 21, 2016

(30) Foreign Application Priority Data
Feb. 28, 2013 (JP) .............................. JP2013-039796

(51) Int. Cl.
*A61B 3/00* (2006.01)
*A61B 3/024* (2006.01)
(Continued)

(52) U.S. Cl.
CPC .......... *A61B 3/0025* (2013.01); *A61B 3/0091* (2013.01); *A61B 3/024* (2013.01); *A61B 3/063* (2013.01); *G16H 50/20* (2018.01)

(58) Field of Classification Search
None
See application file for complete search history.

(56) References Cited

U.S. PATENT DOCUMENTS

| 4,818,091 A | 4/1989 | Sadun et al. |
| 6,033,076 A | 3/2000 | Braeuning et al. |

(Continued)

FOREIGN PATENT DOCUMENTS

| CN | 101966075 A | 2/2011 |
| CN | 102265310 A | 11/2011 |

(Continued)

OTHER PUBLICATIONS

Lesmes, Luis Andres et al., "Bayesian adaptive estimation of the contrast sensitivity function: The quick CSF method", Journal of Vision (2010) 10(3): 17, pp. 1-21.*

(Continued)

*Primary Examiner* — Matthew Kremer (57) ABSTRACT

A visual field test assistance apparatus infers a current visual field status at each test point. A predetermined mixture distribution is applied to a prior-distribution, and parameters regarding the predetermined mixture distribution are learned with reference to time-series information of visual field test results obtained in the past regarding a plurality of cases. The visual field test assistance apparatus calculates an inference test result vector representing an inference result of visual sensitivity to be obtained by the visual field test at each test point, by Bayesian inference, and performs an information output process on the basis of the inference test result vector obtained by the inference.

5 Claims, 1 Drawing Sheet

(51) Int. Cl.
 *G16H 50/20* (2018.01)
 *A61B 3/06* (2006.01)

(56) References Cited

U.S. PATENT DOCUMENTS

| | | |
|---|---|---|
| 6,606,577 B1 | 8/2003 | Fukuhara |
| 2010/0007851 A1 | 1/2010 | Lu et al. |
| 2010/0290006 A1 | 11/2010 | Flanagan et al. |
| 2011/0194075 A1 | 8/2011 | Weleber et al. |
| 2012/0038596 A1 | 2/2012 | Tsuta |
| 2014/0118685 A1 | 5/2014 | Kawamura |
| 2015/0150444 A1* | 6/2015 | Bex .................. A61B 3/0025 351/242 |

FOREIGN PATENT DOCUMENTS

| | | |
|---|---|---|
| CN | 102499623 A | 6/2012 |
| CN | 102793530 A | 11/2012 |
| CN | 102905609 A | 1/2013 |
| JP | 2012-506761 A | 3/2012 |
| WO | 2010/013594 A1 | 2/2010 |
| WO | 2010/053800 A2 | 5/2010 |

OTHER PUBLICATIONS

"Bayesian inference," Wikipedia, https://en.wikipedia.org/wiki/Bayesian_inference, printed on Apr. 16, 2021, 15 pages (Year: 2021).*
European Patent Office, Extended European Search Report for EP patent application No. 13876498.0, dated Sep. 30, 2016.
Written Opinion of the International Searching Authority for PCT/JP2013/073426, dated Oct. 1, 2013.
State Intellectual Property Office of the People's Republic of China, Office Action for Chinese patent application No. 201380074073.9, dated Jul. 28, 2016.
State Intellectual Property Office of the People's Republic of China, Search Report for Chinese patent application No. 201380074073.9, dated Jul. 28, 2016.
International Search Report for PCT/JP2013/073426, dated Oct. 1, 2013.
Viswanathan AC, Fitzk e FW, Hitchings RA. Early Detection of Visual Field Progression in Glaucoma: A Comparison of PROGRESSOR and Statpac2. Br J Ophthalmol 1997; 81(12): 1037-1042.
Hiroshi Murata, Chihiro Mayama, "Gankai no Tameno Sentan Iryo Dai 148 Kai Shiya no Atarasii Tokeigakuteki Kaiseki Hoho", Apr. 30, 2013, pp. 509-511, Journal of the Eye, vol. 30, No. 4.

* cited by examiner

VISUAL FIELD TEST ASSISTANCE APPARATUS

TECHNICAL FIELD

The present disclosure relates to a visual field test assistance apparatus which assists a visual field test of eyesight.

BACKGROUND ART

As a visual field test performed for diagnosing diseases such as glaucoma, etc., there is a known testing method of arranging a plurality of test points within an assumed visual field, lighting each of the test points at a designated luminance, and asking the patient as to whether or not he/she can see the light. Such a testing method may be the Humphrey visual field test.

In such a visual field test method, the processes of changing luminance and obtaining the patient's reactions thereto, must be performed at each of a large number of test points. Therefore, a great burden is imposed not only on the patient, but also on the testing personnel.

A technology for inferring the change of the visual field of a glaucoma patient is disclosed in Viswanathan A C, Fitzke F W, Hitchings R A. Early Detection of Visual Field Progression in Glaucoma: A Comparison of PROGRESSOR and Statpac2. Br J Ophthalmol 1997; 81(12): 1037-1042.

SUMMARY

As mentioned above, decreasing the burden in the visual field test has been desired. Specifically, a visual field test assistance apparatus capable of inferring the status of the current visual field at each test point has been desired.

The present disclosure has been made in view of the above, and one of the objectives of the present disclosure is to provide a visual field test assistance apparatus capable of estimating the status of the current visual field at each test point.

In order to solve the above drawbacks of the prior arts, the present disclosure provides apparatus which assists a visual field test testing visual sensitivity at each of a plurality of test points arranged within a previously assumed visual field range, the apparatus comprising, an acquisition device which acquires parameters regarding a predetermined mixture distribution, the parameters being learned with reference to time-series information of visual field test results obtained in the past regarding a plurality of cases using said mixture distribution for a prior-distribution, an inference calculation device which calculates an inference test result vector representing an inference result of visual sensitivity to be obtained by the visual field test at each test point, by Bayesian inference, by applying a mixture distribution using the acquired parameters to a prior-distribution, and an output device which performs an information output process on the basis of the inference test result vector obtained by the inference, wherein, during the visual field test, when a visual sensitivity is obtained regarding at least one test point by the time of an inference process, the inference calculation device performs a process of updating the prior-distribution by acquiring the visual sensitivity at the test point, and executing Bayesian inference regarding a partial inference test result vector representing an inference result of visual sensitivity at a test point at which no test result has been obtained at the time of the process, and the output device performs an information output process on the basis of the partial inference test result vector.

According to the present disclosure, an inference result of the current visual sensitivity can be obtained.

EMBODIMENT

An embodiment of the present disclosure will be explained with reference to the drawings. A visual field test assistance apparatus 1 according to an embodiment of the present disclosure can be realized by a computer, and specifically, comprises a control unit 11, a storage unit 12, an operation unit 13, a display unit 14, and an input/output unit 15, as exemplified in FIG. 1.

Figure 1:
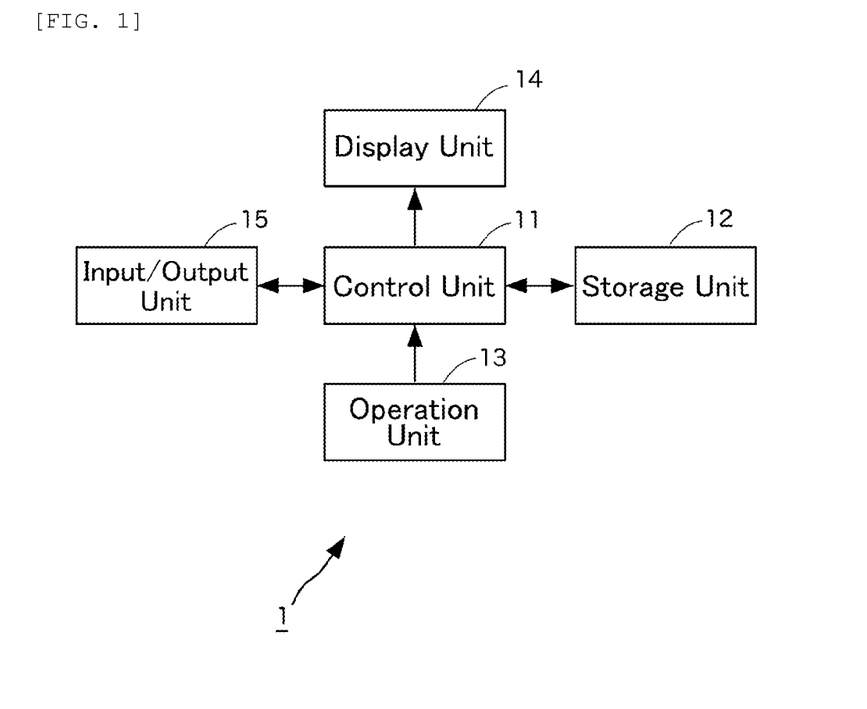
FIG. 1 is a block diagram showing a constitutional example of a visual field test assistance apparatus according to the present disclosure.

Here, the control unit 11 is a program controlled device such as a CPU, etc., and operates in accordance with a program stored in the storage unit 12. According to the present embodiment, the control unit 11 executes a current visual field inference process assisting a visual field test testing visual sensitivity at each of a plurality of test points arranged within a previously assumed visual field range, and a future visual field inference process. In the current visual field inference process, a predetermined mixture distribution is employed as the prior-distribution, time-series information of visual field test results regarding a plurality of cases obtained in the past is referred to, and parameters regarding the applied mixture distribution is learned and stored. Then, the control unit 11 uses a mixture distribution using the learned parameters as a prior-distribution, performs Bayesian inference (specifically, inference by Bayesian linear regression) to calculate an inference test result vector expressing the inference results of visual sensitivities at the respective test points, i.e., the results assumed to be obtained through the visual field tests, and executes an information output process on the basis of the inference test result vector obtained through the Bayesian inference. The process will be described in detail later below.

Further, during the visual field test, when the visual sensitivity information obtained at a test point by the time of the inference process is input through the input/output unit 15, the control unit 11 updates the prior-distribution by the obtained partial visual sensitivity information, and performs inference by Bayesian linear regression to obtain a partial inference test result vector expressing the inference results of visual sensitivities at the test points at which the visual sensitivities have not been obtained at the time of the inference process. Then, the control unit 11 executes the information output process on the basis of the obtained partial inference test result vector.

The control unit 11 also performs a future visual field inference process which includes acquiring time-variable information of visual sensitivities at respective test points, and executing a regression analysis process regarding the acquired time-varied information of visual sensitivities at respective test points. Here, the control unit 11 counts the number of the test points at which the p value for the slope obtained by the regression analysis process is lower than a predetermined analysis threshold value, with respect each of the analysis threshold values, performs a binomial test regarding each of the counted numbers of the test points, and calculates binomial test p values which are the results of the binomial tests. The control unit 11 subjects the calculated binomial test p values to an averaging process, and calculates an averaged binomial test p value, determines presence or absence of a change in the visual sensitivity by referring to whether or not the averaged binomial test p value is lower than a predetermined binominal test threshold value, and outputs a result of the determination. The processes of the control unit 11 will also be described later below.

The storage unit 12 is a memory device, a disk device, etc., which holds a program to be executed by the control unit 11. The program may be provided by being stored in a computer-readable non-transitory medium, and copied to the storage unit 12. Further, the storage unit 12 stores information, such as a parameter value, which is necessary for the processes by the control unit 11. The storage unit 12 also functions as a work memory for the control unit 11.

The operation unit 13 includes a keyboard, a mouse, and the like. The operation unit 13 receives a user's instruction operation, and outputs the content of the instruction operation to the control unit 11. The display unit 14 is a display, a printer, and the like, which outputs information in accordance with the instruction input from the control unit 11.

The input/output unit 15 is a serial or parallel interface which performs data input/output. The input/output unit 15 receives information from an external apparatus, and outputs the received information to the control unit 11. Also, in accordance with instructions input from the control unit 11, the input/output unit 15 outputs information to an external apparatus.

Here, the current visual field inference process by the control unit 11 will be explained. In the following explanation, the current visual field inference result is modelled as a probability variable (random variable) which is shown in Formula (1) below, using the matrix Tm (m representing an identifier identifying an eye to be tested, and satisfying m=1, 2, . . . , M), the matrix Tm representing the result of the visual field test, and being a matrix of the number of test points Dt by the number of tests Nm.

[Numerical Formula 1]

$$P(T_m | w_m, \lambda_m, L_m) = \prod_{n \in n_m} \mathcal{N}(t_n | \Phi(x_n)w_m, \lambda_m^{-1} L_m^{-1}) \quad (1)$$

ただし、

$$\Phi(x_n) = \begin{pmatrix} 1 \\ x_n \end{pmatrix} \otimes I_{D_t}$$

In Formula (1), wm is a vector with an intercept and a slope expressing the visual field progression, L represents a precision matrix (inverse matrix of a variance-covariance matrix), and λ represents a scalar value determining a degree of precision. The symbol of the encircled x represents a Kronecker product.

$$\mathcal{N}(.|.) \quad \text{[Numerical Formula 2]}$$

represents a multivariate normal distribution. Further, xn represents time which has passed from the initial test, and IDt represents the identity matrix having dimensions of Dt×Dt.

Further, the vector wm with an intercept and a slope expressing the visual field progression is described by a mixture normal distribution represented by Formulae (2) and (3).

[Numerical Formula 3]

$$P(w_m | z_m, \lambda_m) = \prod_{k=1}^{K} \{\mathcal{N}(w_m || \mu_k, \lambda_m \Lambda_k)\}^{z_{mk}} \quad (2)$$

$$P(z_m) = \prod_{k=1}^{K} \pi^{z_{mk}} \quad (3)$$

The precision matrix L is also described using a predetermined mixture distribution. For example, the precision matrix L can be described by a mixture of Wishart distributions as represented by Formulae (4) and (5).

[Numerical Formula 4]

$$P(L_m | \zeta_m) = \prod_{h=1}^{H} \{\mathcal{W}(L_m | \nu_h, W_h)\}^{\zeta_{mh}} \quad (4)$$

$$P(\zeta_m) = \prod_{h=1}^{H} \eta_h^{\zeta_{mh}} \quad (5)$$

The scalar value λ representing a degree of precision can be described by, for example, a mixture gamma distribution, as represented by Formulae (6) and (7).

[Numerical Formula 5]

$$P(\lambda) = \prod_{g=1}^{G} \{\mathcal{G}(\lambda_m | a_g, b_g)\}^{\gamma_{mg}} \quad (6)$$

$$P(\gamma_m) = \prod_{g=1}^{G} \theta_g^{\gamma_{mg}} \quad (7)$$

In the above explanation,

[Numerical Formula 6]

$$z_{mk} \in \{0, 1\}$$

$$\sum_{k=1}^{K} z_{mk} = 1$$

$$\zeta_{mh} \in \{0, 1\}$$

$$\sum_{h=1}^{H} \zeta_{mh} = 1$$

are satisfied.

Such mixture distributions are applied, taking into account the experimental knowledge that visual field loss does not always occur at one location, but may occur at a plurality of locations.

Based on the above, likelihood including latent variables, i.e., $$P(T,w,\lambda,L,\zeta,z,\gamma) \quad \text{[Numerical Formula 7]}$$

is described as the product of a sequence of the products of these mixture distributions, the number of the products in the sequence being the number of eyes, specifically, as represented by Formula (*).

[Numerical Formula 8]

$$P(T, w, \lambda, L, \zeta, z, \gamma) = \prod_{m=1}^{M} P(T_m | w_m, \lambda_m, L_m) \quad (*)$$

$$\prod_{m=1}^{M} P(L_m | \zeta_m) \prod_{m=1}^{M} P(\zeta_m)$$

$$\prod_{m=1}^{M} P(w_m | z_m, \lambda_m) \prod_{m=1}^{M} P(z_m)$$

$$\prod_{m=1}^{M} P(\lambda_m) \prod_{m=1}^{M} P(\gamma_m)$$

Prior to the current visual field test result inference process, the control unit 11 uses a formula obtained by assigning Formulae (1) to (6) to Formula (*), to infer the following parameters (hyperparameters).

$$v, W, \mu, \Lambda, a, b, \pi, \theta, \eta \qquad \text{[Numerical Formula 9]}$$

Specifically, the EM Algorithm can be used for this inference for parameters.

When using the EM Algorithm, calculating $$P(w, \lambda, L, z, \zeta, \gamma | T) \qquad \text{[Numerical Formula 10]}$$

in E-step (step for calculating an expectation value for the likelihood) is difficult. The expectation value may be calculated by applying the mean field approximation as below.

$$P(w, \lambda, L, z, \zeta, \gamma | T) = q(w)q(\lambda)q(L)q(\zeta)q(z)q(\gamma) \quad \text{[Numerical Formula 11]}$$

The optimal posterior distribution in the mean field approximation is represented by applying an asterisk (*) as upper index of each symbol. Nm represents the number of tests regarding the eye m, and Dw represents the dimension of the vector $\mu_m$.

Thus, each optimal posterior distribution is represented as below.

$$q^*(w_m) = N(w_m | \hat{\mu}_m, \hat{\Lambda}_m^{-1}) \qquad \text{[Numerical Formula 12]}$$

wherein,

[Numerical Formula 13]

$$\hat{\Lambda}_m = \langle \lambda_m \rangle \left\{ \sum_{n \in n_m} \Phi(x_n) \langle L_m \rangle \Phi(x_n)^T + \sum_{k=1}^{K} \langle z_{mk} \rangle \Lambda_k \right\}$$

$$\hat{\mu}_m = \left\{ \sum_{n \in n_m} \Phi(x_n) \langle L_m \rangle \Phi(x_n)^T + \sum_{k=1}^{K} \langle z_{mk} \rangle \Lambda_k \right\}^{-1}$$

$$\left\{ \sum_{n \in n_m} \Phi(x_n) \langle L_m \rangle t_n + \sum_{k=1}^{K} \langle z_{mk} \rangle \Lambda_k \mu_k \right\}$$

wherein Φ satisfies the equation shown with Formula (1).

$$q^*(\lambda_m) = G(\lambda_m | \hat{a}_m, \hat{b}_m) \qquad \text{[Numerical Formula 14]}$$

wherein,

[Numerical Formula 15]

$$\hat{a}_m = \frac{N_m D_t}{2} + \frac{D_w}{2} + \sum_{g=1}^{G} \langle \gamma_{mg} \rangle a_g$$

$$\hat{b}_m = \sum_{g=1}^{G} \langle \gamma_{mg} \rangle b_g + \frac{1}{2} \sum_{n \in n_m} (t_n - \Phi(x_n)^T \hat{\mu}_m)^T \langle L_m \rangle (t_n - \Phi(x_n)^T \hat{\mu}_m)$$

$$+ \frac{1}{2} \sum_{n \in n_m} \text{Trace}(\hat{\Lambda}_m^{-1} \Phi(x_n) \langle L_m \rangle \Phi(x_n)^T)$$

$$+ \frac{1}{2} \sum_{k=1}^{K} \langle z_{mk} \rangle (\hat{\mu}_m - \mu_k)^T \Lambda_k (\hat{\mu}_m - \mu_k)$$

$$+ \frac{1}{2} \sum_{k=1}^{K} \langle z_{mk} \rangle \text{Trace}(\hat{\Lambda}_m^{-1} \Lambda_k)$$

$$q^*(L_m) = W(L_m | \hat{v}_m, \hat{W}_m) \qquad \text{[Numerical Formula 16]}$$

wherein,

[Numerical Formula 17]

$$\hat{v}_m = \sum_{h=1}^{H} \langle \zeta_{mh} \rangle v_h + N_m$$

$$\hat{W}_m^{-1} = \sum_{h=1}^{H} \langle \zeta_{mh} \rangle W_h^{-1} + \sum_{n \in n_m} \langle \lambda_m \rangle (t_n - \Phi(x_n)^T \hat{\mu}_m)(t_n - \Phi(x_n)^T \hat{\mu}_m)^T +$$

$$\sum_{n \in n_m} \langle \lambda_m \rangle \Phi(x_n)^T \hat{\Lambda}_m^{-1} \Phi(x_n)$$

[Numerical Formula 18]

$$q*(z_m) = \prod_{k=1}^{K} r_{mk}^{z_{mk}}$$

wherein,

[Numerical Formula 19]

$$\ln r_{mk} = \frac{1}{2} \ln |\Lambda_k| - \frac{1}{2} \langle \lambda_m \rangle (\hat{\mu}_m - \mu_k)^T \Lambda_k (\hat{\mu}_m - \mu_k) -$$

$$\frac{1}{2} \langle \lambda_m \rangle \text{Trace}(\hat{\Lambda}_m^{-1} \Lambda_k) + \ln \pi_k + const \sum_{k=1}^{K} r_{mk} = 1$$

[Numerical Formula 20]

$$q*(\zeta_m) = \prod_{h=1}^{H} \rho_{mh}^{\zeta_{mh}}$$

wherein,

[Numerical Formula 21]

$$\ln \rho_{mh} = -\frac{1}{2} v_h \ln |W_h| - \frac{1}{2} v_h D_t \ln 2 \frac{D_t(D_t-1)}{4} \ln \pi - \sum_{i=1}^{D_t} \ln \Gamma \left( \frac{v_h + 1 - i}{2} \right) +$$

$$\frac{v_h - D_t - 1}{2} \langle \ln |L_m| \rangle - \frac{1}{2} \text{Trace}(W_h^{-1} \langle L_m \rangle) + \ln \eta_h + const \sum_{h=1}^{H} \rho_{mh} = 1$$

[Numerical Formula 22]

$$q*(\gamma_m) = \prod_{g=1}^{G} s_{mg}^{\gamma_{mg}}$$ (1.37)

$$b_g^{new} = \frac{a_g \sum_{m=1}^{M} \langle \gamma_{mg} \rangle}{\sum_{m=1}^{M} \langle \gamma_{mg} \rangle \langle \lambda_m \rangle}$$

wherein,

[Numerical Formula 23]

$$\ln s_{mg} = -\ln\Gamma(a_g) + a_g \ln b_g + (a_g - 1)\langle \ln\lambda_m \rangle - b_g \langle \lambda_m \rangle + \ln\theta_g + const \sum_{g=1}^{G} s_{mg} = 1$$

$$\pi_k^{new} = \frac{\sum_{m=1}^{M} \langle z_{mk} \rangle}{M}$$ (1.38)

$$\eta_h^{new} = \frac{\sum_{m=1}^{M} \langle \zeta_{mh} \rangle}{M}$$ (1.39)

$$\theta_g^{new} = \frac{\sum_{m=1}^{M} \langle \gamma_{mg} \rangle}{M}$$ (1.40)

Here, the following equations are satisfied.

With respect to νh, the solution of the following equation is determined as new νh.

[Numerical Formula 24]

$$\langle \lambda_m \rangle = \frac{\hat{a}_m}{\hat{b}_m}$$

$$\langle \ln\lambda_m \rangle = \psi(\hat{a}_m) - \ln\hat{b}_m$$

$$\langle L_m \rangle = \hat{v}_m \hat{W}_m$$

$$\langle \ln L_m \rangle = \sum_{i=1}^{D_t} \psi\left(\frac{\hat{v}_m + 1 - i}{2}\right) + D_t \ln 2 + \ln|\hat{W}_m|$$

[Numerical Formula 27]

$$\ln\left|\sum_{m=1}^{M} \langle \zeta_{mh} \rangle \langle L_m \rangle\right| - D_t \ln v_h - D_t \ln\left(\sum_{m=1}^{M} \langle \zeta_{mh} \rangle\right) +$$

$$D_t \ln 2 + \sum_{i=1}^{D_t} \psi\left(\frac{v_h + 1 - i}{2}\right) - \frac{\sum_{m=1}^{M} \langle \zeta_{mh} \rangle \langle \ln|L_m|\rangle}{\sum_{m=1}^{M} \langle \zeta_{mh} \rangle} = 0$$

$$\langle z_{mk} \rangle = r_{mk}$$

$$\langle \zeta_{mh} \rangle = \rho_{mh}$$

$$\langle \gamma_{mg} \rangle = s_{mg}$$

The new νh is described as $$v_h^{new}$$

With respect to a, the solution of the following equation is determined as new a.

Further, in the M-step (maximization step), hyperparameter re-estimating equations with respect to $$W, \mu, \Lambda, b, \pi, \theta, \eta$$ [Numerical Formula 25]

are as follows.

[Numerical Formula 29]

$$-\psi(a_g) + \ln a_g + \ln\left(\sum_{m=1}^{M} \langle \gamma_{mg} \rangle\right) -$$

[Numerical Formula 26]

$$\mu_k^{new} = \frac{\sum_{m=1}^{M} \langle z_{mk} \rangle \langle \lambda_m \rangle \hat{\mu}_m}{\sum_{m=1}^{M} \langle z_{mk} \rangle \langle \lambda_m \rangle}$$ (1.34)

$$\ln\left(\sum_{m=1}^{M} \langle \gamma_{mg} \rangle \langle L_m \rangle\right) + \frac{\sum_{m=1}^{M} \langle \gamma_{mg} \rangle \langle \ln\lambda_m \rangle}{\sum_{m=1}^{M} \langle \gamma_{mg} \rangle} = 0$$

$$\Lambda_k^{new} = \left\{\sum_{m=1}^{M} \langle z_{mk} \rangle \langle \lambda_m \rangle (\hat{\mu}_m - \mu_k)(\hat{\mu}_m - \mu_k)^T + \sum_{m=1}^{M} \langle z_{mk} \rangle \langle \lambda_m \rangle \hat{\Lambda}_m^{-1}\right\}^{-1} \left(\sum_{m=1}^{M} \langle z_{mk} \rangle\right)$$

The new a is described as $$a_g^{new}$$ [Numerical Formula 30]

In the above equation, ψ(.) represents a digamma function.

As an example, the control unit 11 alternately executes the above E-step and the M-step, and calculates the optimal hyperparameters. The lower bound of the likelihood P(T) can be calculated as below.

[Numerical Formula 31]

$$W_h^{new} = \frac{\sum_{m=1}^{M} \langle \zeta_{mh} \rangle \langle L_m \rangle}{v_h \sum_{m=1}^{M} \langle \zeta_{mh} \rangle}$$ (1.36)

$$\mathcal{LB} = \sum_{m=1}^{M} \sum_{n \in n_m} \mathbb{E}[\ln \mathcal{N}(t_n | \Phi(x_n)w_m, \lambda_m^{-1} L_m^{-1})] +$$

-continued $$\sum_{m=1}^{M}\sum_{h=1}^{H} \mathbb{E}[\zeta_{mh} \ln \mathcal{W}(L_m | v_h, W_h)] + \sum_{m=1}^{M}\sum_{h=1}^{H} \mathbb{E}[\zeta_{mh} \ln \eta_h] +$$

$$\sum_{m=1}^{M}\sum_{k=1}^{K} \mathbb{E}[z_{mk} \ln \mathcal{N}(w_m | \mu_k, \lambda_m^{-1} \Lambda_k^{-1})] +$$

$$\sum_{m=1}^{M}\sum_{k=1}^{K} \mathbb{E}[z_{mk} \ln \pi_k] + \sum_{m=1}^{M}\sum_{g=1}^{G} \mathbb{E}[\gamma_{mg} \ln \mathcal{G}(\lambda_m | a_g, b_g)] +$$

$$\sum_{m=1}^{M}\sum_{g=1}^{G} \mathbb{E}[\gamma_{mg} \ln \theta_g] + -\sum_{m=1}^{M} \mathbb{E}[\ln \mathcal{N}(w_m | \hat{\mu}_m, \hat{\Lambda}_m^{-1})] +$$

$$-\sum_{m=1}^{M} \mathbb{E}[\ln \mathcal{G}(\lambda_m | \hat{a}_m, \hat{b}_m)] + -\sum_{m=1}^{M} \mathbb{E}[\ln \mathcal{W}(L_m | \hat{v}_m, \hat{W}_m)] +$$

$$-\sum_{m=1}^{M}\sum_{k=1}^{K} r_{mk} \ln r_{mk} + -\sum_{m=1}^{M}\sum_{h=1}^{H} \rho_{mh} \ln \rho_{nh} + -\sum_{m=1}^{M}\sum_{g=1}^{G} s_{mg} \ln s_{mg}$$

wherein,

[NumericalFormula 132]

$$\sum_{m=1}^{M}\sum_{n \in n_m} \mathbb{E}[\ln \mathcal{N}(t_n | \Phi(x_n) w_m, \lambda_m^{-1}, L_m^{-1})] =$$

$$-\frac{ND_t}{2} \ln 2\pi + \sum_{m=1}^{M} \left( \frac{N_m D_t}{2} \langle \ln \lambda_m \rangle + \frac{N_m}{2} \langle \ln |L_m| \rangle \right) +$$

$$-\frac{1}{2} \sum_{m=1}^{M} \sum_{n \in n_m} \langle \lambda_m \rangle (t_n - \Phi(x_n)^T \hat{\mu}_m)^T \langle L_m \rangle (t_n - \Phi(x_n)^T \hat{\mu}_m) +$$

$$-\frac{1}{2} \sum_{m=1}^{M} \sum_{n \in n_m} \langle \lambda_m \rangle \mathrm{Trace}\left( \hat{\Lambda}_m^{-1} \Phi(x_n) \langle L_m \rangle \Phi(x_n)^T \right)$$

[NumericalFormula 33]

$$\sum_{m=1}^{M}\sum_{h=1}^{H} \mathbb{E}[\zeta_{mh} \ln \mathcal{W}(L_m | v_h, W_h)] =$$

$$\sum_{h=1}^{H} \left\{ \left( \sum_{m=1}^{M} \langle \zeta_{mh} \rangle \right) \left( -\frac{v_h}{2} \ln |W_h| - \frac{v_h D_t}{2} \ln 2 - \sum_{t=1}^{D_t} \ln \Gamma\left(\frac{v_h + 1 - i}{2}\right) \right) \right\} +$$

$$-\frac{MD_t(D_t - 1)}{4} \ln \pi - \frac{D_t + 1}{2} \sum_{m=1}^{M} \langle \ln |L_m| \rangle +$$

$$\sum_{h=1}^{H} \left\{ \frac{v_h}{2} \sum_{m=1}^{M} \langle \zeta_{mn} \rangle \langle \ln |L_m| \rangle \right\} - \frac{1}{2} \sum_{h=1}^{H} \mathrm{Trace}\left( W_h^{-1} \sum_{m=1}^{M} \langle \zeta_{mh} \rangle \langle L_m \rangle \right)$$

[NumericalFormula 34]

$$\sum_{m=1}^{M}\sum_{h=1}^{H} \mathbb{E}[\zeta_{mh} \ln \eta_h] = \sum_{h=1}^{H} \left\{ \left( \sum_{m=1}^{M} \rho_{mh} \right) \ln \eta_h \right\}$$

[NumericalFormula 35]

$$\sum_{m=1}^{M}\sum_{k=1}^{K} \mathbb{E}[z_{mk} \ln \mathcal{N}(w_m | \mu_k, \lambda_m^{-1} \Lambda_k^{-1})] =$$

$$-\frac{MD_w}{2} \ln 2\pi + \frac{D_w}{2} \sum_{m=1}^{M} \langle \ln \lambda_m \rangle + \frac{1}{2} \sum_{k=1}^{K} \left\{ \left( \sum_{m=1}^{M} \langle z_{mk} \rangle \right) \ln |\Lambda_k| \right\} +$$

$$-\frac{1}{2} \sum_{m=1}^{M} \sum_{k=1}^{K} \langle \lambda_m \rangle \langle z_{mk} \rangle (\hat{\mu}_m - \mu_k)^T \Lambda_k (\hat{\mu}_m - \mu_k) +$$

$$-\frac{1}{2} \sum_{k=1}^{K} \mathrm{Trace}\left( \Lambda_k \sum_{m=1}^{M} \langle z_{mk} \rangle \langle \lambda_m \rangle \hat{\Lambda}_m^{-1} \right)$$

[NumericalFormula 36]

$$\sum_{m=1}^{M}\sum_{k=1}^{K} \mathbb{E}[z_{mk} \ln \pi_k] = \sum_{k=1}^{K} \left\{ \left( \sum_{m=1}^{M} r_{mk} \right) \ln \pi_k \right\}$$

[NumericalFormula 37]

$$\sum_{m=1}^{M}\sum_{g=1}^{G} \mathbb{E}[\gamma_{mg} \ln \mathcal{G}(\lambda_m | a_g, b_g)] =$$

$$\sum_{g=1}^{G} \left\{ \left( \sum_{m=1}^{M} \langle \gamma_{mg} \rangle \right) (-\ln \Gamma(a_g) + a_g \ln b_g) + (a_g - 1) \sum_{m=1}^{M} \langle \gamma_{mg} \rangle \langle \ln \lambda_m \rangle - b_g \sum_{m=1}^{M} \langle \gamma_{mg} \rangle \langle \lambda_m \rangle \right\}$$

[NumericalFormula 38]

$$\sum_{m=1}^{M}\sum_{g=1}^{G} \mathbb{E}[\gamma_{mg} \ln \theta_g] = \sum_{g=1}^{G} \left\{ \ln \theta_g \sum_{g=1}^{G} s_{mg} \right\},$$

$$-\sum_{m=1}^{M} \mathbb{E}\left[ \ln \mathcal{N}(w_m | \hat{\mu}_m, \hat{\Lambda}_m^{-1}) \right] = -\frac{MD_w}{2} \ln 2\pi + \frac{1}{2} \sum_{m=1}^{M} \ln |\hat{\Lambda}_m| - \frac{MD_w}{2},$$

$$-\sum_{m=1}^{M} \mathbb{E}[\ln \mathcal{G}(\lambda_m | \hat{a}_m, \hat{b}_m)] =$$

$$\sum_{m=1}^{M} \left\{ -\ln \Gamma(\hat{a}_m) + (\hat{a}_m - 1) \psi(\hat{a}_m) + \ln \hat{b}_m - \hat{a}_m \right\},$$

$$-\sum_{m=1}^{M} \mathbb{E}[\ln \mathcal{W}(L_m | \hat{v}_m, \hat{W}_m)] =$$

$$\sum_{m=1}^{M} \left\{ -\frac{\hat{v}_m}{2} \ln |\hat{W}_n| - \frac{D_t \hat{v}_m}{2} \ln 2 - \sum_{i=1}^{D_t} \ln \Gamma\left(\frac{\hat{v}_m + 1 - i}{2}\right) \frac{\hat{v}_m - D_t - 1}{2} \langle \ln |L_m| \rangle - \frac{D_t \hat{v}_m}{2} \right\} - \frac{MD_t(D_t - 1)}{4} \ln \pi$$

The control unit 11 stores the optimal hyperparameter values calculated from above, in the storage unit 12.

In response to the instruction, from the operation unit 13, to infer the result of the current visual field test, the control unit 11 executes the following inference process. The inference process is different between (1) the inference process for a patient who has undergone the visual field test for N times before, and (2) the inference process for a patient who undergoes the visual field test for the first time. Therefore, these cases are described separately. The control unit 11 receives instructions indicating the case (1) or the case (2), and executes ether of the following processes.

[For a Patient Who has Undergone the Visual Field Test for N Times Before]

In case of a patient who has undergone the visual field test for N times before, the control unit 11 executes Bayesian inference calculation, provided that the inference test result vector tN+1 indicates an inference result of visual sensitivity at each test point in the current visual field test, that each of the test result vectors t1, t2, . . . , tN indicates each of the past N-time actual measurement results of the visual sensitivity at the each test point, and that the full likelihood of the inference test result vector tN+1 is represented as below.

[Numerical Formula 41]

$$q^*(t_{N+1} \mid w) = \mathcal{N}(t_{N+1} \mid \Phi(x_{N+1})^T w, \langle \lambda \rangle^{-1} \langle L \rangle^{-1}) \quad (8)$$

[Numerical Formula 42]

$$q^*(w) = \mathcal{N}\left(w \mid \hat{\mu}, \hat{\Lambda}^{-1}\right) \quad (9)$$

wherein,

[Numerical Formula 43]

$$\hat{\Lambda} = \langle \lambda \rangle \left\{ \sum_{n=1}^{N} \Phi(x_n) \langle L \rangle \Phi(x_n)^T + \sum_{k=1}^{K} \langle z_k \rangle \Lambda_k \right\}$$

$$\hat{\mu} = \left\{ \sum_{n=1}^{N} \Phi(x_n) \langle L \rangle \Phi(x_n)^T + \sum_{k=1}^{K} \langle z_k \rangle \Lambda_k \right\}^{-1}$$

$$\left\{ \sum_{n=1}^{N} \Phi(x_n) \langle L \rangle \Phi(x_n)^T t_n + \sum_{k=1}^{K} \langle z_k \rangle \Lambda_k \mu_k \right\}$$

[Numerical Formula 44]

$$q^*(\lambda) = \mathcal{G}\left(\lambda \mid \hat{a}, \hat{b}\right) \quad (10)$$

wherein,

[Numerical Formula 45]

$$\hat{a} = \frac{(N+1)D_i}{2} + \frac{D_w}{2} + \sum_{g=1}^{G} \langle \gamma_g \rangle a_g$$

$$\hat{b} = \left\{ \sum_{g=1}^{G} \langle \gamma_g \rangle b_g + \frac{1}{2} \sum_{n=1}^{N} (t_n - \Phi(x_n)^T \hat{\mu})^T \langle L \rangle (t_n - \Phi(x_n)^T \hat{\mu}) + \right.$$

$$\frac{1}{2} \sum_{n=1}^{N} \text{Trace}\left(\hat{\Lambda}^{-1} \Phi(x_n) \langle L \rangle \Phi(x_n)^T\right) +$$

$$\frac{1}{2} \sum_{k=1}^{K} \langle z_k \rangle (\hat{\mu} - \mu_k)^T \Lambda_k (\hat{\mu} - \mu_k) +$$

$$\left. \frac{1}{2} \sum_{k=1}^{K} \langle z_k \rangle \text{Trace}\left(\hat{\Lambda}^{-1} \Lambda_k\right) \left(1 - \frac{D_i}{2\hat{a}}\right)^{-1} \right\} \left(1 - \frac{D_i}{2\hat{a}}\right)^{-1}$$

[Numerical Formula 46]

$$q^*(L) = \mathcal{W}\left(L \mid \hat{v}, \hat{W}\right) \quad (11)$$

wherein,

[Numerical Formula 47]

$$\hat{v} = \sum_{h=1}^{H} \langle \zeta_h \rangle v_h + N + 1 \quad (12)$$

$$\hat{W}^{-1} = \left\{ \sum_{h=1}^{H} \langle \zeta_h \rangle W_h^{-1} + \langle \lambda \rangle \sum_{n=1}^{N} (t_n - \Phi(x_n)^T \hat{\mu})(t_n - \Phi(x_n)^T \hat{\mu})^T + \right.$$

$$\left. \langle \lambda \rangle \sum_{n=1}^{N} \Phi(x_n)^T \hat{\Lambda}^{-1} \Phi(x_n) \right\} \left(1 - \frac{1}{\hat{v}}\right)^{-1}$$

[Numerical Formula 48]

$$q^*(z) = \sum_{k=1}^{K} r_k^{z_k} \quad (12)$$

wherein,

[Numerical Formula 49]

$$\ln r_k = \frac{1}{2} \ln|\Lambda_k| - \frac{\langle \lambda \rangle}{2} (\hat{\mu} - \mu_k)^T \Lambda_k (\hat{\mu} - \mu_k) -$$

$$\frac{\langle \lambda \rangle}{2} \text{Trace}\left(\hat{\Lambda}^{-1} \Lambda_k\right) + \ln \pi_k + const$$

$$\sum_{k=1}^{K} r_k = 1$$

[Numerical Formula 50]

$$q^*(\zeta) = \prod_{h=1}^{H} \rho_h^{\zeta_h} \quad (13)$$

wherein,

[Numerical Formula 51]

$$\ln \rho_h = -\frac{v_h}{2} \ln|W_h| - \frac{v_h D_i}{2} \ln 2 - \frac{D_i(D_i - 1)}{4} \ln \pi - \sum_{i=1}^{D_i} \ln \Gamma\left(\frac{v_h + 1 - i}{2}\right) +$$

$$\frac{v_h - D_i - 1}{2} \langle \ln|L| \rangle - \frac{1}{2} \text{Trace}(W_h^{-1} \langle L_m \rangle) + \ln \eta_h + const$$

$$\sum_{h=1}^{H} \rho_h = 1$$

[Numerical Formula 52]

$$q^*(\gamma) = \prod_{g=1}^{G} s_g^{\gamma_g} \quad (14)$$

wherein,

[Numerical Formula 53]

$$\ln s_g = -\ln \Gamma(a_g) + a_g \ln b_g + (a_g - 1)\langle \ln \lambda \rangle - b_g \langle \lambda \rangle + \ln \theta_g + const$$

$$\sum_{g=1}^{G} s_g = 1$$

Specifically, the posterior distribution after to (n=1, 2, . . . , N) is obtained, is inferred as below, using the mean field approximation $$q(t_{N+1}, w, \lambda, L, z, \zeta, \gamma) = q(t_{N+1}|w)q(w)q(\lambda)q(L)q(z)q(\zeta)q(\gamma) \quad \text{[Numerical Formula 40]}$$

Specifically, the optimal variational posterior distributions are as shown in Formula (8) to Formula (14) below.

[Numerical Formula 41]

$$q^*(t_{N+1}|w) = N(t_{N+1}|\Phi(x_{N+1})^T w, \langle\lambda\rangle^{-1}\langle L\rangle^{-1}) \quad (8)$$

[Numerical Formula 42]

$$q^*(w) = N(w|\hat{\mu}, \hat{\Lambda}^{-1}) \quad (9)$$

wherein,

[NumericalFormula 43]

$$\hat{\Lambda} = \langle\lambda\rangle\left\{\sum_{n=1}^{N}\Phi(x_n)\langle L\rangle\Phi(x_n)^T + \sum_{k=1}^{K}\langle z_k\rangle\Lambda_k\right\}$$

$$\hat{\mu} = \left\{\sum_{n=1}^{N}\Phi(x_n)\langle L\rangle\Phi(x_n)^T + \sum_{k=1}^{K}\langle z_k\rangle\Lambda_k\right\}^{-1}$$

$$\left\{\sum_{n=1}^{N}\Phi(x_n)\langle L\rangle\Phi(x_n)^T t_n + \sum_{k=1}^{K}\langle z_k\rangle\Lambda_k\mu_k\right\}$$

[Numerical Formula 44]

$$q^*(\lambda) = G(\lambda|\hat{a}, \hat{b}) \quad (10)$$

wherein,

[NumericalFormula 45]

$$\hat{a} = \frac{(N+1)D_t}{2} + \frac{D_w}{2} + \sum_{g=1}^{G}\langle\gamma_g\rangle a_g$$

$$\hat{b} = \left\{\sum_{g=1}^{G}\langle\gamma_g\rangle b_g + \frac{1}{2}\sum_{n=1}^{N}(t_n - \Phi(x_n)^T\hat{\mu})^T\langle L\rangle(t_n - \Phi(x_n)^T\hat{\mu}) + \right.$$

$$\frac{1}{2}\sum_{n=1}^{N}\text{Trace}(\hat{\Lambda}^{-1}\Phi(x_n)\langle L\rangle\Phi(x_n)^T) +$$

$$\frac{1}{2}\sum_{k=1}^{K}\langle z_k\rangle(\hat{\mu} - \mu_k)^T\Lambda_k(\hat{\mu} - \mu_k) +$$

$$\left.\frac{1}{2}\sum_{k=1}^{K}\langle z_k\rangle\text{Trace}(\hat{\Lambda}^{-1}\Lambda_k)\left(1 - \frac{D_t}{2\hat{a}}\right)^{-1}\right\}\left(1 - \frac{D_t}{2\hat{a}}\right)^{-1}$$

[Numerical Formula 46]

$$q^*(L) = W(L|\hat{v}, \hat{W}) \quad (11)$$

wherein,

[NumericalFormula 47]

$$\hat{v} = \sum_{h=1}^{H}\langle\zeta_h\rangle v_h + N + 1$$

$$\hat{W}^{-1} = \left\{\sum_{h=1}^{H}\langle\zeta_h\rangle W_h^{-1} + \langle\lambda\rangle\sum_{n=1}^{N}(t_n - \Phi(x_n)^T\hat{\mu})(t_n - \Phi(x_n)^T\hat{\mu})^T + \right.$$

$$\left.\langle\lambda\rangle\sum_{n=1}^{N}\Phi(x_n)^T\hat{\Lambda}^{-1}\Phi(x_n)\right\}\left(1 - \frac{1}{\hat{v}}\right)^{-1}$$

[NumericalFormula 48]

$$q^*(z) = \prod_{k=1}^{K} r_k^{z_k} \quad (12)$$

wherein,

[NumericalFormula 49]

$$\ln r_k = \frac{1}{2}\ln|\Lambda_k| - \frac{\langle\lambda\rangle}{2}(\hat{\mu} - \mu_k)^T\Lambda_k(\hat{\mu} - \mu_k) -$$

$$\frac{\langle\lambda\rangle}{2}\text{Trace}(\hat{\Lambda}^{-1}\Lambda_k) + \ln\pi_k + const \sum_{k=1}^{K} r_k = 1$$

[NumericalFormula 50]

$$q^*(\zeta) = \prod_{h=1}^{H} \rho_h^{\zeta_h} \quad (13)$$

wherein,

[NumericalFormula 51]

$$\ln\rho_h = -\frac{v_h}{2}\ln|W_h| - \frac{v_h D_t}{2}\ln 2 - \frac{D_t(D_t-1)}{4}\ln\pi - \sum_{i=1}^{D_t}\ln\Gamma\left(\frac{v_h+1-i}{2}\right) +$$

$$\frac{v_h - D_t - 1}{2}\langle\ln|L|\rangle - \frac{1}{2}\text{Trace}(W_h^{-1}\langle L_m\rangle) + \ln\eta_k + const\sum_{h=1}^{H}\rho_h = 1$$

[NumericalFormula 52]

$$q^*(\gamma) = \prod_{g=1}^{G} s_g^{\gamma_g} \quad (14)$$

wherein,

[NumericalFormula 53]

$$\ln s_g = -\ln\Gamma(a_g) + a_g\ln b_g + (a_g - 1)\langle\ln\lambda\rangle - b_g\langle\lambda\rangle + \ln\theta_g + const\sum_{g=1}^{G} s_g = 1$$

With this respect, the following are satisfied.

[NumericalFormula 54]

$$\langle\lambda\rangle = \frac{\hat{a}}{\hat{b}}$$

$$\langle\ln\lambda\rangle = \psi(\hat{a}) - \ln\hat{b}$$

$$\langle L\rangle = \hat{v}\hat{W}$$

$$\langle\ln L\rangle = \sum_{i=1}^{D_t}\psi\left(\frac{\hat{v}+1-i}{2}\right) + D_t\ln 2 + \ln|\hat{W}|$$

$\langle z_k \rangle = r_k$ $\langle \zeta_h \rangle = \rho_h$ $\langle \gamma_g \rangle = s_g$ Further, parameters which have been previously calculated and stored in the storage unit 12 are used for $v, W, \mu, \Lambda, a, b, \pi, \theta, \eta$ [Numerical Formula 9]

The inference result of tN+1 that the control unit 11 should obtain, is obtained by Formula (15).

[Numerical Formula 55]

$$q(t_{N+1}) = \int \mathcal{N}(t_{N+1} \mid \Phi(x_{N+1})^T w, \langle \lambda \rangle^{-1} \langle L \rangle^{-1}) \mathcal{N}(w \mid \hat{\mu}, \hat{\Lambda}^{-1}) dw \quad (15)$$
$$= \mathcal{N}(t_{N+1} \mid \Phi(x_{N+1})^T \hat{\mu}, \langle \lambda \rangle^{-1} \langle L \rangle^{-1} + \Phi(x_{N+1})^T \hat{\Lambda}^{-1} \Phi(x_{N+1}))$$

According to the multivariate normal distribution represented by Formula (15), the control unit 11 obtains the inference test result vector tN+1 which indicates an inference result of visual sensitivity at each test point in the current visual field test. Then, the control unit 11 executes an information output process on the basis of the obtained inference result vector tN+1. The information output process will be described below.

In the above calculation, the lower bound of the likelihood P(T) is represented as follows.

[Numerical Formula 56]

$$\mathcal{LB} = \mathbb{E}[\ln \mathcal{N}(t_{N+1} \mid \Phi(x_{N+1})w, \lambda^{-1}L^{-1})] \sum_{n=1}^{N} \mathbb{E}[\ln \mathcal{N}(t_n \mid \Phi(x_n)w, \lambda^{-1}L^{-1})] +$$
$$\sum_{k=1}^{K} \mathbb{E}[z_k \ln \mathcal{N}(w \mid \mu_k, \lambda^{-1}\Lambda_k^{-1})] + \sum_{k=1}^{K} \mathbb{E}[z_k \ln \pi_k] +$$
$$\sum_{h=1}^{H} \mathbb{E}[\zeta_h \ln \mathcal{W}(L \mid v_h, W_h)] + \sum_{n=1}^{H} \mathbb{E}[\zeta_h \ln \eta_h] +$$
$$\sum_{g=1}^{G} \mathbb{E}[\gamma_g \ln \mathcal{G}(\lambda \mid a_g, b_g)] + \sum_{g=1}^{G} \mathbb{E}[\gamma_g \ln \theta_g] +$$
$$- \mathbb{E}[\ln \mathcal{N}(t_{N+1} \mid \Phi(x_{N+1})w, \langle \lambda \rangle^1 \langle L \rangle^1)] +$$
$$- \mathbb{E}[\ln \mathcal{N}(w \mid \hat{\mu}, \hat{\Lambda}^{-1})] + - \mathbb{E}[\ln \mathcal{G}(\lambda \mid \hat{a}, \hat{b})] +$$
$$- \mathbb{E}[\ln \mathcal{W}(L \mid \hat{v}, \hat{W})] + - \sum_{k=1}^{K} r_k \ln r_k + - \sum_{h=1}^{H} \rho_h \ln \rho_h + - \sum_{g=1}^{G} s_g \ln s_g$$

The sum of the 1st and 9th terms is represented as follows.

$$\mathbb{E}[\ln \mathcal{N}(t_{N+1} \mid \Phi(x_{N+1})w, \lambda^{-1}, L^{-1})] - \quad \text{[Numerical Formula 57]}$$
$$\mathbb{E}[\ln \mathcal{N}(t_{N+1} \mid \Phi(x_{N+1})w, \langle \lambda \rangle^{-1}, \langle L \rangle^{-1})] =$$
$$\frac{D_t}{2}(\langle \ln \lambda \rangle - \ln \langle \lambda \rangle) + \frac{1}{2}(\langle \ln |L| \rangle - \ln |\langle L \rangle|)$$

Other terms of the expectation values can be represented as follows.

$$\sum_{n=1}^{N} \mathbb{E}[\ln \mathcal{N}(t_n \mid \Phi(x_n)w, \lambda^1 L^1)] = -\frac{ND_t}{2} \ln 2\pi + \quad \text{[Numerical Formula 58]}$$
$$\frac{ND_t}{2} \langle \ln \lambda \rangle + \frac{N}{2} \langle \ln |L| \rangle + -$$
$$\frac{1}{2} \sum_{n=1}^{N} \langle \lambda \rangle (t_n - \Phi(x_n)^T \hat{\mu})^T \langle L \rangle$$
$$(t_n - \Phi(x_n)^T \hat{\mu}) + -$$
$$\frac{1}{2} \sum_{n=1}^{N} \langle \lambda \rangle Trace(\hat{\Lambda}^1 \Phi(x_n) \langle L \rangle \Phi(x_n)^T)$$

$$\sum_{k=1}^{K} \mathbb{E}[z_k \ln \mathcal{N}(w \mid \mu_k, \lambda^{-1} \Lambda_k^{-1})] = -\frac{D_w}{2} \ln 2\pi + \quad \text{[Numerical Formula 59]}$$
$$\frac{D_w}{2} \langle \ln \lambda_m \rangle + \frac{1}{2} \sum_{k=1}^{K} \langle z_k \rangle \ln |\Lambda_k| + -$$
$$\frac{\langle \lambda \rangle}{2} \sum_{k=1}^{K} \langle z_k \rangle (\hat{\mu} - \mu_k)^T \Lambda_k (\hat{\mu} - \mu_k) -$$
$$\frac{\langle \lambda \rangle}{2} Trace\left(\hat{\Lambda}^{-1} \sum_{k=1}^{K} \langle z_k \rangle \Lambda_k\right),$$
$$\sum_{k=1}^{K} \mathbb{E}[z_k \ln \pi_k] = \sum_{k=1}^{K} r_k \ln \pi_k$$

$$\sum_{h=1}^{H} \mathbb{E}[\zeta_h \ln \mathcal{W}(L \mid v_h, W_h)] = \quad \text{[Numerical Formula 60]}$$
$$\sum_{h=1}^{H} \langle \zeta_h \rangle \left( -\frac{v_h}{2} \ln |W_h| - \frac{v_h D_1}{2} \ln 2 - \right.$$
$$\sum_{i=1}^{D_i} \ln \Gamma\left(\frac{v_h + 1 - i}{2}\right) +$$
$$\left. \frac{v_h - D_i + 1}{2} \langle \ln |L| \rangle \right) -$$
$$\frac{1}{2} Trace\left(\langle L \rangle \sum_{h=1}^{H} \langle \zeta_h \rangle W_h^{-1}\right) -$$
$$\frac{D_t(D_t - 1)}{4} \ln \pi,$$
$$\sum_{n=1}^{H} \mathbb{E}[\zeta_h \ln \eta_k] = \sum_{h=1}^{H} \rho_h \ln \eta_h,$$
$$\sum_{g=1}^{G} \mathbb{E}[\gamma_g \ln \mathcal{G}(\lambda \mid a_g, b_g)] =$$
$$\sum_{g=1}^{G} \langle \gamma_g \rangle (-\ln \Gamma(a_g) + a_g \ln b_g +$$
$$(a_g - 1) \langle \ln \lambda \rangle - b_g \langle \lambda \rangle),$$
$$\sum_{g=1}^{G} \mathbb{E}[\gamma_g \ln \theta_g] = \sum_{g=1}^{G} s_g \ln \theta_g$$

-continued $$-\mathbb{E}[\ln\mathcal{N}(w\,|\,\hat{\mu},\hat{\Lambda}^1)] = \qquad\qquad \text{[Numerical Formula 61]}$$
$$-\frac{D_w}{2}\ln 2\pi + \frac{1}{2}\ln|\hat{\Lambda}| - \frac{D_w}{2},$$

$$-\mathbb{E}[\ln\mathcal{G}(\lambda\,|\,\hat{a},\hat{b})] =$$
$$-\ln\Gamma(\hat{a}) + (\hat{a}-1)\psi(\hat{a}) + \ln\hat{b} - \hat{a},$$

$$-\mathbb{E}[\ln\mathcal{W}(L\,|\,\hat{v},\hat{W})] =$$
$$-\frac{\hat{v}}{2}\ln|\hat{W}| - \frac{D_t\hat{v}}{2}\ln 2 - \sum_{i=1}^{D_t}\ln\Gamma\left(\frac{v+1-i}{2}\right) +$$
$$\frac{\hat{v}-D_t-1}{2}\langle\ln|L|\rangle - \frac{D_t\hat{v}}{2} - \frac{D_t(D_t-1)}{4}\ln\pi$$

Further, the control unit 11 updates the content of the information output during the actual visual field test. Namely, when the visual field test is performed and a part of the actual test results (visual sensitivity information of a part of the test points) is input through the input/output unit 15, the control unit 11 updates the prior-distribution with reference to the visual sensitivity information of the test points which has already been obtained by the time of the inference process. Specifically, the control unit 11 divides the test result vector $t_{N+1}$ into the visual sensitivity information (vector) ta indicating the visual sensitivity information of the test points which has not been obtained by time of the process, and the visual sensitivity information (vector) tb indicating the visual sensitivity information of the test points which has already been obtained by the time of the process. For convenience, the divided elements are represented as $$t = \begin{pmatrix} t_a \\ t_b \end{pmatrix} \qquad\qquad \text{[Numerical Formula 62]}$$

(if the order of measurement is predetermined among the test points, the elements of the vector t may be set in the order of measurement). The corresponding μ and Λ are represented as below.

$$\mu = \begin{pmatrix} \mu_a \\ \mu_b \end{pmatrix} \Lambda = \begin{pmatrix} \Lambda_{aa} & \Lambda_{ab} \\ \Lambda_{ba} & \Lambda_{bb} \end{pmatrix} \qquad \text{[Numerical Formula 63]}$$

Then, the control unit 11 calculates the inference result to of the unmeasured test points as a partial inference test result vector, using the following equation.

$$P(t_a|t_b) = N(t_a|\mu_a - \Lambda_{aa}^{-1}\Lambda_{ab}(t_b-\mu_b), \Lambda_{aa}^{-1}) \qquad \text{[Numerical Formula 64]}$$

Thereby, provided that each of a plurality of unmeasured test points is a noted test point, the inference test result information at the noted test point can be obtained.

The control unit 11 executes an information output process, on the basis of the thus obtained inference result ta(P(ta|tb)). The information output process will be explained later below.

[For a Patient Who Undergoes the Visual Field Test for the First Time]

In case of a patient who undergoes the visual field test for the first time, no past information is present. Therefore, upon receiving instructions to perform inference regarding a patient who undergoes the visual field test for the first time, the control unit 11 infers the posterior distribution which should be the inference result of the visual sensitivity information at each test point, by performing approximate inference using a mixture normal distribution.

Specifically, similar to the case of a patient which has already undergone the visual field test for N times, the full likelihood at the time point 0 is set as the following equation.

$$P(t_0, w, \lambda, L, z, \zeta, \gamma) = \mathcal{N}(t_0\,|\,\Phi(0)w, \lambda^{-1}L^{-1}) \qquad \text{[Numerical Formula 65]}$$

$$\prod_{k=1}^{K}\{\mathcal{N}(w\,|\,\mu_k, \lambda^{-1}\Lambda_k^{-1})\}^{z_k}$$

$$\prod_{k=1}^{K}\pi_k^{z_k}\prod_{h=1}^{H}\{\mathcal{W}(L\,|\,v_h, W_h)\}^{\zeta_h}\prod_{h=1}^{H}\eta_h^{\zeta_h}$$

$$\prod_{g=1}^{G}\mathcal{G}(\lambda\,|\,a_g, b_g)^{\gamma_g}\prod_{g=1}^{G}\theta_g^{\gamma_g}$$

This equation is approximated as $$P(t_0, w, \lambda, L, z, \zeta, \gamma) = q(t_0|w)q(w|z)q(z)q(\lambda)q(\gamma)q(L)q(\zeta) \qquad \text{[Numerical Formula 66]}$$

The control unit 11 obtains a mixture normal distribution to minimize Kullback-Leibler divergence represented by the formula below.

$$-\int q(t_0\,|\,w)q(w\,|\,z)q(z)q(\lambda)q(\gamma)q(L)q(\zeta) \qquad \text{[Numerical Formula 67]}$$
$$\frac{P(t_0, w, \lambda, L, z, \zeta, \gamma)}{q(t_0\,|\,w)q(w\,|\,z)q(z)q(\lambda)q(\gamma)q(L)q(\zeta)}$$
$$d\,t_0 w\lambda L z\zeta\gamma$$

In the mixture normal distribution, $$q^*(t_0\,|\,w) = N(t_0\,|\,\Phi(0)w, \langle\lambda\rangle^{-1}\langle L\rangle^{-1}) \qquad \text{[Numerical Formula 68]}$$

$$q^*(w\,|\,z) = \prod_{k=1}^{K}\{\mathcal{N}(w\,|\,\mu_k, \langle\lambda\rangle^{-1}\Lambda_k^1)\}^{z_k}$$

$$q^*(z) = \prod_{k=1}^{K}\pi_k^{z_k}$$

$$q^*(\lambda) = \mathcal{G}(\lambda\,|\,\hat{a}, \hat{b})$$

wherein, $$\hat{a} = \sum_{g=1}^{G}\langle\gamma_g\rangle a_g + \frac{D_w + D_t}{2} \qquad \text{[Numerical Formula 69]}$$

$$\hat{b} = \left(\sum_{g=1}^{G}\langle\gamma_g\rangle b_g\right)\left(1 - \frac{D_t + D_w}{\hat{a}}\right)^{-1}$$

$$q^*(L) = \mathcal{W}(L\,|\,\hat{v}, \hat{W}) \qquad \text{[Numerical Formula 70]}$$

wherein, $$\hat{v} = \sum_{h=1}^{H}\langle\zeta_h\rangle v_h + 1 \qquad \text{[Numerical Formula 71]}$$

$$\hat{W}^{-1} = \left(\sum_{h=1}^{H}\langle\zeta\rangle W_h^1\right)\left(1 - \frac{1}{\hat{v}}\right)^1$$

-continued $$q^*(\gamma) = \prod_{g=1}^{G} s_g^{z_k}$$ [Numerical Formula 72]

$$q^*(\lambda) = \mathcal{G}(\lambda \mid \hat{a}, \hat{b})$$

wherein, $$\hat{a} = \sum_{g=1}^{G} \langle \gamma_g \rangle a_g + \frac{D_w + D_t}{2}$$ [Numerical Formula 69]

$$\hat{b} = \left(\sum_{g=1}^{G} \langle \gamma_g \rangle b_g\right)\left(1 - \frac{D_t + D_w}{\hat{2}}\right)^{-1}$$

$$q^*(L) = \mathcal{W}(L \mid \hat{v}, \hat{W})$$ [Numerical Formula 70]

wherein, $$\hat{v} = \sum_{h=1}^{H} \langle \zeta_h \rangle v_h + 1$$ [Numerical Formula 71]

$$\hat{W}^{-1} = \left(\sum_{h=1}^{H} \langle \zeta_h \rangle W_h^1\right)\left(1 - \frac{1}{\hat{v}}\right)^{-1}$$

$$q^*(\gamma) = \prod_{g=1}^{G} s_g^{\gamma_g}$$ [Numerical Formula 72]

wherein, $$\ln s_g = \ln\Gamma(a_g) + a_g \ln b_g +$$ [Numerical Formula 73]
$$(a_g - 1)\langle\ln\lambda\rangle - b_g\langle\lambda\rangle + \ln\theta_g + const$$

$$\sum_{g=1}^{G} s_g = 1$$

$$q^*(\zeta) = \prod_{h=1}^{H} \rho_h^{\zeta_h}$$ [Numerical Formula 74]

wherein, $$\ln\rho_h \propto -\frac{v_h}{2}\ln|W_h| - \frac{v_h D_t}{2}\ln 2 - \frac{D_t(D_t-1)}{4}\ln\pi -$$ [Numerical Formula 75]

$$\sum_{i=1}^{D_t} \ln\Gamma\left(\frac{v_h + 1 - i}{2}\right) + \frac{v_h - D_i - 1}{2}\langle\ln|L|\rangle -$$

$$\frac{1}{2}\text{Trace}(W_h^{-1}\langle L_m \rangle) + \ln\eta_h + const$$

$$\sum_{h=1}^{H} \rho_h = 1$$

The control unit 11 uses a predetermined mixture normal distribution function, and appropriately (for example, randomly) sets initial values for the parameters of the function. The control unit 11 repeats the process of calculating the Kullback-Leibler divergence of the mixture normal distribution function, updating the parameters to minimize the Kullback-Leibler divergence, and calculating the Kullback-Leibler divergence again, until the Kullback-Leibler divergence converges. The specific embodiment for this calculation can be a widely known method.

With respect to "t0" which has become the optimal distribution by the above process, the control unit 11 obtains $$q(t_0|w)q(w|z)q(z)$$ [Numerical Formula 76]

Further, the control unit 11 marginalizes the above regarding w and z, to obtain "t0". Specifically, the control unit 11 calculates the following equation to obtain "t0".

$$\sum_z \int q(t_0 \mid w) q(w \mid z) q(z) dw =$$ [Numerical Formula 77]

$$\sum_{k=1}^{K} \pi_k \mathcal{N}(t_{N+1} \mid \Phi(0)\hat{\mu},$$

$$\langle\lambda\rangle^{-1}\langle L \rangle^{-1} + \Phi(0)^T \Lambda_k^{-1}\Phi(0))$$

For these calculations, the control unit 11 uses parameter values stored in the storage unit 12. Further, the Kullback-Leibler divergence at this time can be represented as follows.

$$KL = -\mathbb{E}[\ln\mathcal{N}(t_0 \mid \Phi(x_0)w, \lambda^{-1}L^{-1})] -$$ [Numerical Formula 78]

$$\sum_{k=1}^{K} \mathbb{E}[z_k \ln\mathcal{N}(w \mid \mu_k, \lambda^1 \Lambda_k^1)] + -$$

$$\sum_{k=1}^{K} \mathbb{E}[z_k \ln\pi_k] +$$

$$-\sum_{h=1}^{H} \mathbb{E}[\zeta_h \ln\mathcal{W}(L \mid v_h, W_h)] +$$

$$-\sum_{h=1}^{H} \mathbb{E}[\zeta_h \ln\eta_h] +$$

$$-\sum_{g=1}^{G} \mathbb{E}[\gamma_g \ln\mathcal{G}(\lambda \mid a_g, b_g)] +$$

$$-\sum_{g=1}^{G} \mathbb{E}[\gamma_g \ln\theta_g] +$$

$$\mathbb{E}[\ln\mathcal{N}(t_0 \mid \Phi(x_0)w, \langle\lambda\rangle^{-1}\langle L \rangle^{-1})]$$

$$\sum_{k=1}^{K} \mathbb{E}[z_k \ln\mathcal{N}(w \mid \mu_k, \langle\lambda\rangle^1 \Lambda_k^{-1})] +$$

$$\sum_{k=1}^{K} \mathbb{E}[z_k \ln\pi_k] + \mathbb{E}[\ln\mathcal{G}(\lambda \mid \hat{a}, \hat{b})] +$$

$$\mathbb{E}[\ln\mathcal{W}(L \mid \hat{v}, \hat{W})] + \sum_{h=1}^{H} \rho_h \ln\rho_h + \sum_{g=1}^{G} s_g \ln s_g$$

Here, the 3rd term and 10th term cancel to each other. The sum of the 1st term and the 8th term is represented as $$-\mathbb{E}[\ln\mathcal{N}(t_0 \mid \Phi(x_0)w, \lambda^{-1}, L^{-1})] +$$ [Numerical Formula 79]

$$\mathbb{E}[\ln\mathcal{N}(t_0 \mid \Phi(x_0)w, \langle\lambda\rangle^{-1}, \langle L \rangle^{-1})] =$$

$$\frac{D_t}{2}(\ln\langle\lambda\rangle - \langle\ln\lambda\rangle) + \frac{1}{2}(\ln|\langle L \rangle| - \langle\ln|L|\rangle)$$

The sum of the 2nd term and the 9th term is represented as $$-\sum_{k=1}^{K} \mathbb{E}[z_k \ln\mathcal{N}(w \mid \mu_k, \lambda^{-1}\Lambda_k^{-1})] +$$ [Numerical Formula 80]

-continued $$\sum_{k=1}^{K} \mathbb{E}[z_k \ln \mathcal{N}(w \mid \mu_k, \langle \lambda \rangle^{-1} \Lambda_k^{-1})] =$$

$$\frac{D_w}{2}(\ln\langle\lambda\rangle - \langle \ln\lambda\rangle).$$

The expectation values for the 4th term to the 7th term, the 11th term, and the 12th term can be represented as below, respectively.

[Numerical Formula 81]

$$-\sum_{h=1}^{H} \mathbb{E}[\zeta_h \ln \mathcal{W}(L \mid v_h, W_h)] =$$

$$\sum_{h=1}^{H} \langle \zeta_h \rangle \Biggl( -\frac{v_h}{2}\ln|W_h| - \frac{v_h D_t}{2}\ln 2 -$$

$$\sum_{i=1}^{D_t} \ln\Gamma\left(\frac{v_h + 1 - i}{2}\right) +$$

$$\frac{v_h - D_t + 1}{2}\langle \ln|L|\rangle \Biggr) -$$

$$\frac{1}{2}\mathrm{Trace}\Biggl(\langle L\rangle \sum_{h=1}^{H} \langle \zeta_h\rangle W_h^{-1}\Biggr) -$$

$$\frac{D_t(D_t - 1)}{4}\ln\pi,$$

$$-\sum_{h=1}^{H} \mathbb{E}[\zeta_h \ln \eta_h] = \sum_{h=1}^{H} \rho_h \ln \eta_h,$$

$$-\sum_{g=1}^{G} \mathbb{E}[\gamma_g \ln \mathcal{G}(\lambda \mid a_g, b_g)] =$$

$$\sum_{g=1}^{G} \langle \gamma_g\rangle(-\ln\Gamma(a_g) + a_g \ln b_g +$$

$$(a_g - 1)\langle\ln\lambda\rangle - b_g\langle\lambda\rangle),$$

$$-\sum_{g=1}^{G} \mathbb{E}[\gamma_g \ln \theta_g] = \sum_{g=1}^{G} s_g \ln \theta_g,$$

$$\mathbb{E}[\ln \mathcal{G}(\lambda \mid \hat{a}, \hat{b})] =$$

$$-\ln\Gamma(\hat{a}) + (\hat{a} - 1)\psi(\hat{a}) + \ln\hat{b} - \hat{a},$$

$$\mathbb{E}[\ln \mathcal{W}(L \mid \hat{v}, \hat{W})] =$$

$$-\frac{\hat{v}}{2}\ln|\hat{W}| - \frac{D_t \hat{v}}{2}\ln 2 - \sum_{i=1}^{D_t}\ln\Gamma\left(\frac{v + 1 - i}{2}\right) +$$

$$\frac{\hat{v} - D_t - 1}{2}\langle \ln|L|\rangle - \frac{D_t \hat{v}}{2} - \frac{D_t(D_t - 1)}{4}\ln\pi$$

The control unit 11 executes an information output process on the basis of the thus obtained t0. The information output process will be described later below.

Further, the control unit 11 updates the content of the information output during the actual visual field test for a patient who undergoes the visual field test for the first time. Namely, when the visual field test is performed and a part of the actual test results (visual sensitivity information of a part of the test points) is input through the input/output unit 15, the control unit 11 updates the prior-distribution with reference to the visual sensitivity information of the test points which has already been obtained by the time of inference process. Specifically, the control unit 11 divides the test result vector t into the visual sensitivity information (vector) to indicating the visual sensitivity information of the test points which has not been obtained by time of the process, and visual sensitivity information (vector) tb indicating the visual sensitivity information of the test points which has already been obtained by the time of the process. For convenience, the divided elements are represented as $$t = \begin{pmatrix} t_a \\ t_b \end{pmatrix}$$ [Numerical Formula 62]

(if the order of measurement is predetermined among the test points, the elements of the vector t may be sent in the order of measurement). The corresponding μ and Λ are represented as below.

$$\mu_k = \begin{pmatrix} \mu_{k,a} \\ \mu_{k,b} \end{pmatrix}$$ [Numerical Formula 82]

$$\Lambda_k = \begin{pmatrix} \Lambda_{k,aa} & \Lambda_{k,ab} \\ \Lambda_{k,ba} & \Lambda_{k,bb} \end{pmatrix}$$

Then, the control unit 11 calculates the inference result to of a part of the test points as a partial inference test result vector, using the following equation.

$$P(t_a \mid t_b) = \sum_{k=1}^{K} \pi_k^{new}$$ [Numerical Formula 83]

$$\mathcal{N}(t_a \mid \mu_{k,a} - \Lambda_{k,aa}^{-1}\Lambda_{k,ab}(t_b - \mu_{k,b}), \Lambda_{k,aa}^{-1})$$

wherein, $$\pi_k^{new} \propto \pi_k \sqrt{\frac{|\Lambda_k|}{|\Lambda_{k,aa}|}} \exp$$ [Numerical Formula 84]

$$\left\{-\frac{1}{2}(t_b - \mu_{k,b})^T(\Lambda_{k,bb} - \Lambda_{k,ba}\Lambda_{k,aa}^{-1}\Lambda_{k,ab})\right.$$

$$\left.(t_b - \mu_{k,b})\right\} \sum_{k=1}^{K} \pi_k^{new} = 1$$

Thereby, provided that each of a plurality of unmeasured test points is a noted test point, the inference test result information at the noted test point can be obtained.

The control unit 11 executes an information output process, on the basis of the thus obtained inference result ta(P(ta|tb)). The information output process will be explained below.

[Information Output Process]

The control unit 11 executes an information output process, after obtaining an inference test result vector or a partial inference test result vector, including the inference results of the visual sensitivity at unmeasured test points, as described above. In the information output process, for example, the control unit 11 may display a list including information for specifying respective test points as well as the visual sensitivity inference results of at least a part of the relevant test points (unmeasured test points) included in the inference test result vector or the partial inference test result vector, as they are.

Thereby, a testing personnel can obtain information regarding the luminance which is inferred to be visible for a patient at a predetermined probability, and can select a luminance to be initially presented to the patient at each test point, with reference to the luminance indicated by the information as probably visible. Accordingly, the number of trials to present a luminance which is definitely visible for the patient, can be decreased, resulting in decreasing the number of repetitions at each test point, and reducing the burden of the test for both the testing personnel and the patient.

Further, selecting a test result at a noted test point, the noted test point being one of the unmeasured test points, from the test results included in the inference test result vector or the partial inference test result vector, the control unit 11 may execute the following process. Namely, the control unit 11 calculates a difference between the inference result at the noted test point and the inference result or the measurement result (actual test result) of the visual sensitivity at a test point neighboring to the noted test point, and when the calculated difference exceeds a predetermined threshold value for spatial change, the control unit 11 outputs information for specifying a neighbor space of the noted test point.

Figure 2:
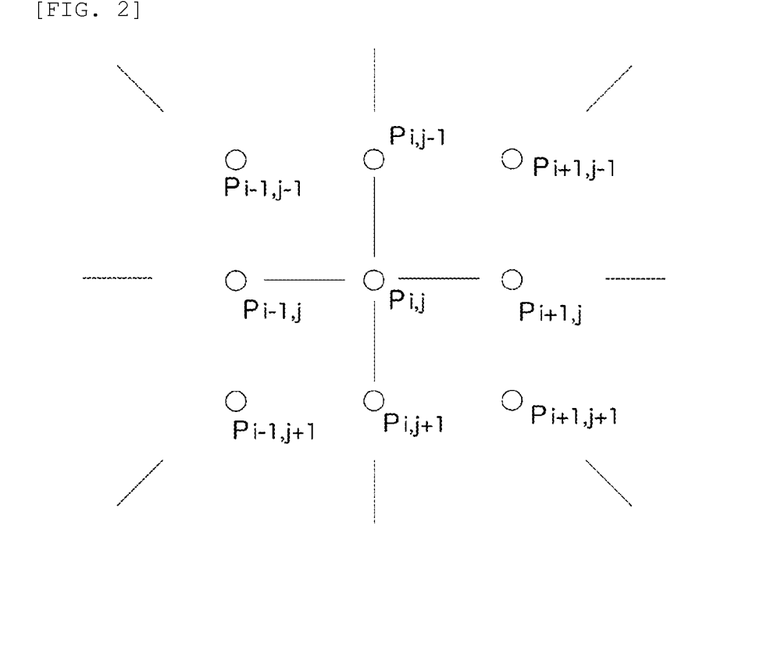
FIG. 2 is an explanatory view showing an example of arranging test points used in the process of a visual field test assistance apparatus according to the present disclosure.

As shown in FIG. 2, for example, provided that there are an unmeasured test point $P_{i,j}$, and test points $P_{i-1,j}$, $P_{i,j-1}$, $P_{i+1,j}$, $P_{i,j+1}$ (usually referred to as 4-neighbor test points) which have been previously set adjacent to the test point $P_{i,j}$, and that inferred visual sensitivity values for these test points are $V[P_{i,j}]$, $V[P_{i-1,j}]$, $V[P_{i,j-1}]$, $V[P_{i+1,j}]$, $V[P_{i,j+1}]$, respectively, the control unit 11 calculates the difference between the value at the test point $P_{i,j}$ and each of the values at the 4-neighbor test points, the differences being $\Delta i|1,j=|V[P_{i-1,j}]-P_{i,j}|$, $\Delta i,j-1=|V[P_{i,j-1}]-P_{i,j}|$, $\Delta i+1,j=|V[P_{i+1,j}]-P_{i,j}|$, $\Delta i,j+1=|V[P_{i,j+1}]-P_{i,j}|$ (wherein, $|*|$ refers to an absolute value of $*$).

When any of the calculated differences exceeds a predetermined threshold value (referred to as spatial change threshold value), the control unit 11 outputs information which specifies a neighbor space of the noted test point $P_{i,j}$, to the display unit 14. At this time, the control unit 11 may also display, on the display unit 14, a suggestion to arrange more test points within the specified space. Here, specifically, the neighbor space of the noted test point $P_{i,j}$ may be the position of the noted test point $P_{i,j}$ itself. The neighbor space of the noted test point $P_{i,j}$ may also be a range of space within a predetermined distance r from the noted test point $P_{i,j}$, and the like.

Referring to the display, the testing personnel may arrange more test points within the displayed range or around the displayed position, in accordance with need, and perform the measurement at these test points. Thereby, more accurate testing becomes possible.

[Future Inference]

The visual field test assistance apparatus 1 according to the present embodiment may infer the result of a future visual field test, and output the inference result thereof, as described below. In this case, with respect to a designated patient, the control unit 11 receives the results of the tests undergone by the patient in the past. The received test results include the visual sensitivity information of a plurality of time points in the past, regarding each test point.

With respect to each test point, the control unit 11 executes a regression analysis process regarding the change in the visual sensitivity over time indicated by the information acquired as above, to thereby obtain values for an intercept and a slope as well as p values therefor, regarding the change. The control unit 11 counts the number of test points where the p value for the slope is lower than a predetermined analysis threshold value (where the change of test result over time progresses). Also, the control unit 11 executes a one-sided binomial test regarding the counted number of test points, to calculate a result of the binomial test, i.e., a binomial test p value (a probability that the number of test points is not significant). With respect to the number of test points where the progression occurs, the prior ratio of such test points should be obtained in advance.

The control unit 11 sets the analysis threshold value to a plurality of values which are different from each other, and repeats the above process regarding the plurality of analysis threshold values. Here, the analysis threshold values are set to, for example, four values, i.e., 0.025, 0.5, 0.075, and 0.1. The control unit 11 calculates an averaged binomial test p value, by averaging the binomial test p values obtained corresponding to the respective analysis threshold values (specifically, the median of the binomial test p values may be used). When the averaged binomial test p value is lower than a predetermined test threshold value, the control unit 11 determines that the visual sensitivity change over time is significant (the change in the test result (visual sensitivity) progresses over time). Then, the control unit 11 outputs the determination result regarding the presence/absence of the change in the visual sensitivity over time, to the display unit 14.

When the control unit 11 determines the visual sensitivity change over time is present, the control unit 11 displays a position, within the visual field space, of a test point having a p value (p value relating to the slope of the regression analysis result) lower than a predetermined analysis threshold value. Thereby, the location of the test point inferred as having a visual sensitivity change over time is provided. Then, on the basis of the regression analysis result with respect to each test point determined as having a visual sensitivity change over time, the control unit 11 obtains an inference result of the visual field at a designated time point in the future, and outputs the obtained inference result. This process is performed by assigning the regression analysis result and time until the designated time point to a regression formula, with respect to each test point determined as having a visual sensitivity change over time, and obtaining and displaying the visual sensitivity information at each test point.

Accordingly, a portion where progression in visual sensitivity occurs, and a future visual sensitivity at the relevant portion, can be provided. Thus, the testing personnel and the patient can obtain an inference result regarding a visual field test result to be obtained in the future. In this case, for example, a medical staff can specifically point out the future situation while taking the living conditions of the patient into account, resulting in contributing the decision on treatment, etc.

[Operation]

The visual field test assistance apparatus 1 according to the present embodiment has a structure as above, and operates as follows. Namely, the visual field test assistance apparatus 1 performs Bayesian inference using a predetermined mixture distribution for the prior-distribution, and infers a result of a current or future visual field test as a posterior distribution. At this time, parameters relating to the mixture distribution have been obtained in advance, through a learning process using known information, i.e., measurement results of a plurality of occasions (time-series information measured with time intervals), regarding a plurality of patients measured in the past.

At the time of the test, in case of a patient who underwent the test in the past, the visual field test assistance apparatus 1 performs Bayesian inference using information of the patient's past test result and the mixture distribution using the previously obtained parameters, and infers a visual field test result of the current test (information of luminance which is inferred to be visible for a patient at a predetermined probability at each test point). Then, the visual field test assistance apparatus 1 provides the inference result to the testing personnel. The testing personnel refers to the luminance information, and determines a luminance to be initially presented to the patient regarding each unmeasured test point.

During the test, the testing personnel inputs luminance information obtained at each test point through the test, to the visual field test assistance apparatus 1 (or the device used for the test may be set to input the relevant information, without requiring any human-made operations). When the visual field test assistance apparatus 1 receives the luminance information obtained during the test at a test point, the visual field test assistance apparatus 1 updates the prior-distribution using the received information, and infers a visual field test result at an unmeasured test point by Bayesian inference. Then, the visual field test assistance apparatus 1 provides a newly inferred result to the testing personnel. The testing personnel refers to the newly inferred result and determines a luminance which should be initially presented to the patient at the unmeasured test point.

In case of a patient who undergoes the test for the first time, a similar processes are performed by executing inference using a predetermined mixture normal distribution. Thereby, unlike the case where test results are obtained through trials and errors, the testing personnel can set initial conditions on the basis of a test result having a predetermined probability, and thus, test results can be obtained in a comparatively short time.

Modified Example

In the above explanation, the visual field test assistance apparatus 1 calculates a difference between an inference result of visual sensitivity at a test point (noted test point) and an inference result or a measurement result (actual test result) of visual sensitivity at a neighbor test point, and when the calculated difference exceeds a predetermined spatial change threshold value, the visual field test assistance apparatus 1 outputs information specifying a neighbor space of the noted test point. With this respect, the spatial change threshold value does not have to be the same value over the entirety of the visual field space.

For example, it is well known that the test result values of the test points arranged in the upper half of the visual field space are little related to the test result values of the test points arranged in the lower half of the visual field space. With respect to a pair of test points respectively arranged on the upper half and the lower half of the visual field space, the space change threshold value to be used for the comparison with the difference between the pair of test points may be set greater, compared to the space change threshold value to be used for the comparison for the test points located in other part.

Further, in the visual field test assistance apparatus 1 explained above, one set of parameters is used for the Bayesian inference. However, parameters may be divided into a plurality of groups on the basis of race, sex, residence, etc., and parameters may be obtained for respective groups through learning using test results of patients belonging to respective groups.

In this case, the visual field test assistance apparatus 1 infers the test result regarding a patient to be inferred, by selecting parameters obtained through learning on the basis of patient information belonging to a group same as the group to which the relevant patient to be inferred belongs.

The invention claimed is:

1. A visual field test assistance apparatus which assists a tester who performs a visual field test of a subject, the apparatus comprising:

a processor which acquires parameters of a predetermined mixture distribution used in Bayesian inference, the parameters being learned with reference to visual field test result information obtained through the visual field test in the past, the visual field test result information including information of visual sensitivity information obtained at each of a plurality of test points arranged within a previously assumed visual field range, sets the predetermined mixture distribution with the acquired parameters to a prior-distribution for the Bayesian inference, for the subject who undergoes the visual field test for a first time, sets posterior distribution by using a predetermined mixture normal distribution function, and repeats a step of calculating a Kullback-Leibler divergence of the predetermined mixture normal distribution function and updating the parameters to minimize the Kullback-Leibler divergence, until the Kullback-Leibler divergence converges for the Bayesian inference, obtains the visual sensitivity information at each of the plurality of test points by time of an inference process through an input/output unit during the visual field test, each time the visual sensitivity information at one or more of the plurality of the test points arranged within the previously assumed visual field range is obtained, updates the prior-distribution using the obtained visual sensitivity information, calculates a partial inference test result vector representing a Bayesian inference result of the visual sensitivity information with taking advantage of the prior-distribution and the posterior distribution to be obtained by the visual field test at a test point at which no test result has been obtained at a time of the process of calculating the partial inference test result vector, by the Bayesian inference, and performs an information output process on a basis of the partial inference test result vector obtained by the Bayesian inference, wherein the processor causes an output unit to output a list including information for specifying visual sensitivity inference results of at least a part of the partial inference test result vector which represents inferred visual sensitivity at unmeasured test points.

2. A visual field test assistance apparatus according to claim 1, wherein, in the information output process on a basis of an inference test result vector obtained by the Bayesian inference, or on the basis of the partial inference test result vector representing the Bayesian inference result of the visual sensitivity information at the test point—at which no test result has been obtained at the time of the process of calculating the partial inference test result vector, the processor calculates information of a luminance inferred to be visible for a patient at a predetermined probability at the test point at which no test result has been obtained, on the basis of the inference test result vector or the partial inference test result vector, and outputs information for specifying the test point at which no test result has been obtained and the calculated information of the luminance to be visible for the patient at the predetermined probability at the test point at which no test result has been obtained.

3. A visual field test assistance apparatus according to claim 1, wherein, in the information output process on a basis of an inference test result vector obtained by the Bayesian inference, or the information output process on the basis of the partial inference test result vector representing the Bayesian inference result of the visual sensitivity information at the test point at which no test result has been obtained at the time of the process of calculating the partial inference test result vector, the processor calculates a difference between the Bayesian inference result of the visual sensitivity information at the test point at which no test result has been obtained and that of a measurement result of visual sensitivity information at a test point neighboring to the test point at which no test result has been obtained, on the basis of the inference test result vector or the partial inference test result vector, and outputs information for specifying a neighboring space of the test point at which no test result has been obtained when the calculated difference exceeds a predetermined spatial change threshold value.

4. A visual field test assistance apparatus according to claim 1, wherein the processor acquires visual sensitivity change information over time at each test point, performs a regression analysis process in which the acquired visual sensitivity change information over time at each test point is analyzed, counts a number of test points at which a p value for a slope obtained by the regression analysis process is lower than a predetermined analysis threshold value, sets a plurality of mutually different values as analysis threshold values for an estimation of the acquired visual sensitivity change information over time by the regression analysis process, executes a binomial test using the number of test points relative to the respective analysis threshold values, and calculates binomial test p values as results of the binomial test using the number of test points relative to the respective analysis threshold values, executes an averaging process in which averaging of the calculated binomial test p values corresponding to the respective analysis threshold values is performed, and determines presence/absence of a visual sensitivity change on a basis of whether or not the averaged binomial test p value is lower than a predetermined test threshold value, and outputs a result of a determination of the presence/absence of the visual sensitivity change.

5. A visual field test assistance apparatus according to claim 4, wherein the processor outputs a visual field inference result by the Bayesian inference at a designated time point in the future on a basis of a spatial arrangement of test points determined to have the visual sensitivity change, and the slope obtained by the regression analysis process.

* * * * *